(12) United States Patent
Izui et al.

(10) Patent No.: US 7,973,222 B1
(45) Date of Patent: Jul. 5, 2011

(54) METHOD TO CONFER FORMALDEHYDE-RESISTANCE TO A PLANT, AND A METHOD TO HAVE A PLANT ABSORB ENVIROMENTAL FORMALDEHYDE

(75) Inventors: Katsura Izui, Kyoto (JP); Limei Chen, Kyoto (JP); Nobuo Kato, Kyoto (JP); Yasuyoshi Sakai, Kyoto (JP); Hiroya Yurimoto, Kyoto (JP)

(73) Assignee: Katsura Izui, Kita-Ku, Kyoto (JP)

( * ) Notice: Subject to any disclaimer, the term of this patent is extended or adjusted under 35 U.S.C. 154(b) by 793 days.

(21) Appl. No.: 10/581,861

(22) PCT Filed: Dec. 3, 2004

(86) PCT No.: PCT/JP2004/018665
§ 371 (c)(1),
(2), (4) Date: Mar. 3, 2008

(87) PCT Pub. No.: WO2005/054474
PCT Pub. Date: Jun. 16, 2005

(30) Foreign Application Priority Data

Dec. 5, 2003 (JP) ................. 2003-407508

(51) Int. Cl.
*C12N 15/31* (2006.01)
*C12N 15/52* (2006.01)
*C12N 15/82* (2006.01)
*A01H 5/00* (2006.01)

(52) U.S. Cl. ............ 800/317.3; 800/288; 800/298; 800/306; 800/317

(58) Field of Classification Search .............. None
See application file for complete search history.

(56) References Cited

OTHER PUBLICATIONS

Achkor, H. et al. Plant Physiology (Aug. 2003) vol. 132; pp. 2248-2255.*
Mitsui, R. et al. Journal of Bacteriology, Feb. 2000, vol. 182, No. 4; pp. 944-948.*
Yurimoto, H. et al. FEMS Microbiology Letters, 2002, vol. 214; pp. 189-193.*

Supplemental European Search Report, European Patent Application No. 04807024.7-1212, dated Mar. 10, 2008.
Hakima Achkor et al., "Enhanced formaldehyde detoxification by overexpression of glutathione-dependent formaldehyde dehydrogenase from Arabidopsis", Plant Physiology, vol. 132, No. 4, Aug. 2003, pp. 2248-2255, XP002470346.
Database EMBL [Online], Feb. 4, 2000 "Mycobacterium gastri MB19 formaldehyde-fixing operon genes (orfl, rmpB, rmpA, rmpD), partial and complete cds." XP002470349.
Heribert Schmitz et al., "Assimilation and metabolism of formaldehyde by leaves appear unlikely to be of value for indoor air purification", New Phytologist, vol. 147, No. 2, Aug. 2000, pp. 307-315, XP002470347.
Martina Giese et al., "Detoxification of formaldehyde by the spider plant (Chlorophytum comosum L.) cell-suspension cultures", Plant Physiology, vol. 104, No. 4, 1994, pp. 1301-1309, XP002470348.
Izumi Orita et al., "Bifunctional enzyme fusion of 3-hexulose-6-phosphate synthase and 6-phospho-3-hexuloisomerase", Applied Microbiology and Biotechnology, Springer-Verlag, BE, vol. 76, No. 2, May 23, 2007, pp. 439-445, XP019538684.
L. Chen et al., "Installation of formaldehyde-fixation pathway of methylotroph as a bypass of carboxylation step of the Calvin cycle in higher plants", Photosynthesis Research, Dordrecht, NL, vol. 91, No. 2-3, Feb. 2007, pp. 234-234, XP008088718.
Chen LM, et al., Assimilation of formaldehyde in transgenic plants due to the introduction of the bacterial ribulose monophosphate pathway genes. Biosci Biotechnol Biochem. Mar. 23, 2010, 74(3):627-35. Epub Mar. 7, 2010, PubMed PMID: 20208346.
Song Z et al., Overexpression of an HPS/PHI fusion enzyme from Mycobacterium gastri in chloroplasts of geranium enhances its ability to assimilate and phytoremediate formaldehyde. Biotechnol Lett. Jun. 15, 2010, [Epub ahead of print] PubMed PMID:20549541.

* cited by examiner

*Primary Examiner* — Russell Kallis
(74) *Attorney, Agent, or Firm* — Buchanan Ingersoll & Rooney PC

(57) ABSTRACT

According to this invention, by introducing genes encoding hexulose-6-phosphate synthase and 6-phosphohexulose isomerase into a plant to have the genes expressed in the chloroplast of the plant, a transgenic plant having a pathway to assimilate formaldehyde through the Calvin cycle is provided. The transgenic plant according to this invention has resistance to formaldehyde and is capable of reducing the level of environmental formaldehyde significantly. Therefore, it is assumed that the transgenic plant according to this invention can be used to purify environmental condition, by placing it in a residence or in an office.

16 Claims, 14 Drawing Sheets
(5 of 14 Drawing Sheet(s) Filed in Color)

FIG. 5

Primer for amplification of rmpA gene by PCR rmpA-sense (2506-2530)    GCATGCAAGGGGTAACCATGACG rmpA-antisense (3150-3129)    TCTAGAGGATCAGGCGATCGC Sequence of transit peptide (accession:X05986)      atg
```
301 gcttcttcag taatgtcctc agcagctgtt gccacccgcg gcaatggtgc acaagctagc
361 atggttgcac ccttcactgg actcaagtcc accgcttctt tccctgtttc aaggaagcaa
421 aaccttgaca ttacctccat tgctagcaac ggtggaagag tcagttgc
```
Sequence of rmpA gene (accession: AB034913)      atg
```
2521 aagctccaag tcgccatcga cctgctgtcc accgaagccg ccctcgagct ggccggcaag
2581 gttgccgagt acgtcgacat catcgaactg ggcaccccc tgatcgaggc cgagggcctg
2641 tcggtcatca ccgccgtcaa gaaggctcac ccggacaaga tcgtcttcgc cgacatgaag
2701 accatggacg ccggcgagct cgaagccgac atcgcgttca aggccggcgc tgacctggtc
2761 acggtcctcg gctcggccga cgactccacc atcgcgggtg ccgtcaaggc cgcccaggct
2821 cacaacaagg gcgtcgtcgt cgacctgatc ggcatcgagg acaaggccac ccgtgcacag
2881 gaagttcgcg ccctgggtgc caagttcgtc gagatgcacg ctggtctgga cgagcaggcc
2941 aagcccggct tcgacctgaa cggtctgctc gccgccggcg agaagctcg cgttccgttc
3001 tccgtggccg gtggcgtgaa agttgcgacc atccccgcag tccagaaggc cggcgcagaa
3061 gttgccgtcg ccggtggcgc catctacggt gcagccgacc cggccgccgc cgcgaaggaa
3121 ctgcgcgccg cgatcgcctg atcctgatcg
```
                                                                                                Cleavage site MASSVMSSAAVATRGNGAQASMVAPFTGLKSTASFPVSRKQNLDITSIASNGGRVSC      MKLQVAID
LLSTEAALELAGKVAEYVDIIELGTPLIEAEGLSVITAVKKAHPDKIVFADMKTMDAGELEADIAFKAGADL
VTVLGSADDSTIAGAVKAAQAHNKGVVVDLIGIEDKATRAQEVRALGAKFVEMHAGLDEQAKPGFDLNGLLA
AGEKARVPFSVAGGVKVATIPAVQKAGAEVAVAGGAIYGAADPAAAAKELRAAIA

FIG. 6

DNA sequence used for vector construction
Primer for amplification of rmpB gene by PCR rmpB-sense (1825-1850)     GCATGCAAGGGGTAACCATGACG rmpB-antisense (2456-2435) TCTAGATCCGGGTCACTCGAG Sequence of transit peptide    (accession:X05986)
                                                                                   atg
301 gcttcttcag taatgtcctc agcagctgtt gccacccgcg gcaatggtgc acaagctagc
361 atggttgcac ccttcactgg actcaagtcc accgcttctt tccctgtttc aaggaagcaa
421 aaccttgaca ttacctccat tgctagcaac ggtggaagag tcagttgc
Sequence of rmpB gene (accession: AB034913)
                                                                              atgacg caagccgcag
1861 aagccgacgg cgccgtgaag gtcgtcggag acgacatcac caacaacctt tcccttgttc
1921 gggacgaggt cgcggacacc gcggcgaaag tcgacccgga gcaggtggct gtcctcgctc
1981 gccaaatcgt ccagcctgga cgggttttcg tggcgggcgc cggtcgcagc gggctcgtcc
2041 tgcgcatggc cgccatgcgg ctgatgcact tcggcctcac cgtgcacgtc gcgggcgaca
2101 ccaccacccc ggcaatctca gccggcgatc tgctgctggt ggcttccggc tgggcacca
2161 cctccggtgt ggtcaagtcc gccgagacgg ccaagaaggc cggggcgcgc atcgccgcct
2221 tcaccaccaa cccggattct ccgctggccg gtctggccga cgccgtggtg atcatcccg
2281 ccgcgcagaa gaccgatcac ggctcgcaca tttcgcggca gtacgccgga tcccttttcg
2341 agcaggtgct gttcgtcgtc accgaagccg tgttccagtc gctgtgggat cacaccgagg
2401 tcgaggccga ggaactctgg acgcgccacg ccaactcga gtgacccgga cctcga Cleavage site
MASSVMSSAAVATRGNGAQASMVAPFTGLKSTASFPVSRKQNLDITSIASNGGRVSMTQAAEADGAVK
VVGDDITNNLSLVRDEVADTAAKVDPEQVAVLARQIVQPGRVFVAGAGRSGLVLRMAAMRLMHFGLTVH
VAGDTTTPAISAGDLLLVASGSGTTSGVVKSAETAKKAGARIAAFTTNPDSPLAGLADAVVIIPAAQKT
DHGSHISRQYAGSLFEQVLFVVTEAVFQSLWDHTEVEAEELWTRHANLE

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: PRIMER

<400> SEQUENCE: 1
gcttgcaagg ggtaaccatg acg           23

<210> SEQ ID NO 2
<211> LENGTH: 21
<212> TYPE: DNA
<213> ORGANISM: Artificial Sequence
<220> FEATURE:
<223> OTHER INFORMATION: PRIMER

<400> SEQUENCE: 2
tctagaggat caggcgatcg c             21

<210> SEQ ID NO 3
<211> LENGTH: 23
<212> TYPE: DNA
<213> ORGANISM: Artificial Sequence
<220> FEATURE:
<223> OTHER INFORMATION: PRIMER

<400> SEQUENCE: 3
gcttgcaagg ggtaaccatg acg           23

<210> SEQ ID NO 4
<211> LENGTH: 21
<212> TYPE: DNA
<213> ORGANISM: Artificial Sequence
<220> FEATURE:
<223> OTHER INFORMATION: PRIMER

<400> SEQUENCE: 4
tctagatccg ggtcactcga g             21

<210> SEQ ID NO 5
<211> LENGTH: 171
<212> TYPE: DNA
<213> ORGANISM: Lycopersicon esculentum

<400> SEQUENCE: 5
atggcttctt cagtaatgtc ctcagcagct gttgccaccc gcggcaatgg tgcacaagct      60
agcatggttg caccctcac tggactcaag tccaccgctt ctttccctgt ttcaaggaag      120
caaaaccttg acattacctc cattgctagc aacggtggaa gagtcagttg c             171

<210> SEQ ID NO 6
<211> LENGTH: 633

```
<212> TYPE: DNA
<213> ORGANISM: Mycobacterium gastri

<400> SEQUENCE: 6
atgaagctcc aagtcgccat cgacctgctg tccaccgaag ccgccctcga gctggccggc      60
aaggttgccg agtacgtcga catcatcgaa ctgggcaccc ccctgatcga ggccgagggc     120
ctgtcggtca tcaccgccgt caagaaggct caccccggaca agatcgtctt cgccgacatg    180
aagaccatgg acgccggcga gctcgaagcc gacatcgcgt tcaaggccgg cgctgacctg     240
gtcacggtcc tcggctcggc cgacgactcc accatcgcgg gtgccgtcaa ggccgcccag    300
gctcacaaca agggcgtcgt cgtcgacctg atcggcatcg aggacaaggc cacccgtgca    360
caggaagttc gcgccctggg tgccaagttc gtcgagatgc acgctggtct ggacgagcag    420
gccaagcccg gcttcgacct gaacggtctg ctcgccgccg gcgagaaggc tcgcgttccg    480
ttctccgtgg ccggtggcgt gaaagttgcg accatccccg cagtccagaa ggccggcgca    540
gaagttgccg tcgccggtgg cgccatctac ggtgcagccg acccggccgc cgccgcgaag    600
gaactgcgcg ccgcgatcgc ctgatcctga tcg                                  633

<210> SEQ ID NO 7
<211> LENGTH: 633
<212> TYPE: DNA
<213> ORGANISM: Mycobacterium gastri

<400> SEQUENCE: 7
atgaagctcc aagtcgccat cgacctgctg tccaccgaag ccgccctcga gctggccggc      60
aaggttgccg agtacgtcga catcatcgaa ctgggcaccc ccctgatcga ggccgagggc     120
ctgtcggtca tcaccgccgt caagaaggct caccccggaca agatcgtctt cgccgacatg    180
aagaccatgg acgccggcga gctcgaagcc gacatcgcgt tcaaggccgg cgctgacctg     240
gtcacggtcc tcggctcggc cgacgactcc accatcgcgg gtgccgtcaa ggccgcccag    300
gctcacaaca agggcgtcgt cgtcgacctg atcggcatcg aggacaaggc cacccgtgca    360
caggaagttc gcgccctggg tgccaagttc gtcgagatgc acgctggtct ggacgagcag    420
gccaagcccg gcttcgacct gaacggtctg ctcgccgccg gcgagaaggc tcgcgttccg    480
ttctccgtgg ccggtggcgt gaaagttgcg accatccccg cagtccagaa ggccggcgca    540
gaagttgccg tcgccggtgg cgccatctac ggtgcagccg acccggccgc cgccgcgaag    600
gaactgcgcg ccgcgatcgc ctgatcctga tcg                                  633

<210> SEQ ID NO 8
<211> LENGTH: 57
<212> TYPE: PRT
<213> ORGANISM: Artificial sequence
<220> FEATURE:
<223> OTHER INFORMATION: rbcS3C

<400> SEQUENCE: 8

Met Ala Ser Ser Val Met Ser Ser Ala Ala Val Ala Thr Arg Gly Asn
1               5                  10                   15

Gly Ala Gln Ala Ser Met Val Ala Pro Phe Thr Gly Leu Lys Ser Thr
            20                  25                  30

Ala Ser Phe Pro Val Ser Arg Lys Gln Asn Leu Asp Ile Thr Ser Ile
        35                  40                  45

Ala Ser Asn Gly Gly Arg Val Ser Cys
    50                  55
```

```
<210> SEQ ID NO 9
<211> LENGTH: 207
<212> TYPE: PRT
<213> ORGANISM: Artificial sequence
<220> FEATURE:
<223> OTHER INFORMATION: rmpA

<400> SEQUENCE: 9

Met Lys Leu Gln Val Ala Ile Asp Leu Leu Ser Thr Glu Ala Ala Leu
1               5                   10                  15

Glu Leu Ala Gly Lys Val Ala Glu Tyr Val Asp Ile Ile Glu Leu Gly
            20                  25                  30

Thr Pro Leu Ile Glu Ala Glu Gly Leu Ser Val Ile Thr Ala Val Lys
        35                  40                  45

Lys Ala His Pro Asp Lys Ile Val Phe Ala Asp Met Lys Thr Met Asp
50                  55                  60

Ala Gly Glu Leu Glu Ala Asp Ile Ala Phe Lys Ala Gly Ala Asp Leu
65                  70                  75                  80

Val Thr Val Leu Gly Ser Ala Asp Ser Thr Ile Ala Gly Ala Val
                85                  90                  95

Lys Ala Ala Gln Ala His Asn Lys Gly Val Val Asp Leu Ile Gly
            100                 105                 110

Ile Glu Asp Lys Ala Thr Arg Ala Gln Glu Val Arg Ala Leu Gly Ala
        115                 120                 125

Lys Phe Val Glu Met His Ala Gly Leu Asp Glu Gln Ala Lys Pro Gly
130                 135                 140

Phe Asp Leu Asn Gly Leu Leu Ala Gly Glu Lys Ala Arg Val Pro
145                 150                 155                 160

Phe Ser Val Ala Gly Gly Val Lys Val Ala Thr Ile Pro Ala Val Gln
                165                 170                 175

Lys Ala Gly Ala Glu Val Ala Val Ala Gly Gly Ala Ile Tyr Gly Ala
            180                 185                 190

Ala Asp Pro Ala Ala Ala Lys Glu Leu Arg Ala Ala Ile Ala
        195                 200                 205

<210> SEQ ID NO 10
<211> LENGTH: 199
<212> TYPE: PRT
<213> ORGANISM: Artificial sequence
<220> FEATURE:
<223> OTHER INFORMATION: rmpB

<400> SEQUENCE: 10

Met Thr Gln Ala Ala Glu Ala Asp Gly Ala Val Lys Val Val Gly Asp
1               5                   10                  15

Asp Ile Thr Asn Asn Leu Ser Leu Val Arg Asp Glu Val Ala Asp Thr
            20                  25                  30

Ala Ala Lys Val Asp Pro Glu Gln Val Ala Val Leu Ala Arg Gln Ile
        35                  40                  45

Val Gln Pro Gly Arg Val Phe Val Ala Gly Ala Gly Arg Ser Gly Leu
50                  55                  60

Val Leu Arg Met Ala Ala Met Arg Leu Met His Phe Gly Leu Thr Val
65                  70                  75                  80

His Val Ala Gly Asp Thr Thr Thr Pro Ala Ile Ser Ala Gly Asp Leu
                85                  90                  95

Leu Leu Val Ala Ser Gly Ser Gly Thr Thr Ser Gly Val Val Lys Ser
            100                 105                 110

Ala Glu Thr Ala Lys Lys Ala Gly Ala Arg Ile Ala Ala Phe Thr Thr
```

-continued

```
            115                 120                 125
Asn Pro Asp Ser Pro Leu Ala Gly Leu Ala Asp Ala Val Ile Ile
        130                 135                 140

Pro Ala Ala Gln Lys Thr Asp His Gly Ser His Ile Ser Arg Gln Tyr
145                 150                 155                 160

Ala Gly Ser Leu Phe Glu Gln Val Leu Phe Val Val Thr Glu Ala Val
                165                 170                 175

Phe Gln Ser Leu Trp Asp His Thr Glu Val Glu Ala Glu Glu Leu Trp
                180                 185                 190

Thr Arg His Ala Asn Leu Glu
        195
```

METHOD TO CONFER FORMALDEHYDE-RESISTANCE TO A PLANT, AND A METHOD TO HAVE A PLANT ABSORB ENVIROMENTAL FORMALDEHYDE

BACKGROUND OF THE INVENTION

1. Field of the Invention

This invention relates to a method to confer formaldehyde-resistance to a plant comprising the steps of; introducing gene(s) encoding enzyme(s) involved in the metabolic system of formaldehyde into the plant and having the gene(s) expressed in the chloroplast, thereby the ability to assimilate formaldehyde into an intermediate of the Calvin cycle is conferred to said plant, and to a transgenic plant produced by the method. Moreover, this invention relates to a method to have a plant to absorb environmental formaldehyde comprising the steps of; introducing gene(s) encoding enzyme(s) involved in the metabolic system of formaldehyde into the plant and having the gene(s) expressed in the chloroplast, thereby the ability to assimilate formaldehyde into an intermediate of the Calvin cycle is conferred to said plant, and to a transgenic plant produced by the method.

2. Background Art

Formaldehyde is a chemical substance existing in building materials etc., and it is known to cause sick house syndrome, because formaldehyde effects to human body even if the concentration in the atmosphere is very low. The regulation of environmental standard of formaldehyde is expected to become stricter than before, for example, the use of building materials which release formaldehyde is prohibited according to the amendment of Building Standard Law dated Jul. 1, 2003. Therefore, in view of decreasing the amount of substances involved in environmental pollution (for example phytoremediation using a plant), a method available to remove and to decrease the concentration of environmental formaldehyde has been demanded.

Meanwhile, as a technique to decrease the concentration of environmental formaldehyde by a biological means, a method using a microorganism that can degrade formaldehyde has been known. However, until now, a technique to decrease formaldehyde concentration using a transgenic plant has not been known, which comprising production of the transgenic plant introduced with a gene encoding an enzyme involved in metabolic system of a plant. Moreover, despite that there have been techniques to confer resistance to various stresses to a plant by performing gene recombination in a plant, there has not been an example to incorporate a gene involved in metabolic system, in view of environmental purification.

Meanwhile, as an example of environmental purification using a plant, a method to clean-up dioxin containing medium is known, and the method is characterized in that Ri plasmid derived from *Agrobacterium rhizogenes* is introduced into a plant of *Solanaceae, Cruciferae, Umbelliferae, Chenopodiaceae, Leguminosae, Compositae*, or *Saxifragaceae* to induce the hairy root of the plant, and contacting it with the dioxin containing medium to have the dioxin absorbed or decomposed by the hairy root or by the re-generated plant body (Japanese Patent Publication No. 2000-176433). However, this report is not directed to formaldehyde.

In addition, as a knowledge on the formaldehyde metabolism of a plant, it has been reported that a plant body, in which the expression of glutathione-dependent formaldehyde dehydrogenase (FALDH) derived from *Arabidopsis thaliana* is manipulated, has been produced (Plant Physiol. 2003). As a result, the intake of formaldehyde was enhanced in a plant body in which FALDH was over-expressed, whereas the intake of formaldehyde was apparently low in a wild-type plant body in which the expression of FALDH had not been manipulated. From this result, it is apparently suggested that FALDH is involved in detoxification of formaldehyde.

Meanwhile, among microorganisms, existence of methylotrophic microorganisms, which can grow using a compound having one carbon (C1 compound) such as methanol has been known. Such microorganism is provided with a metabolic pathway that serves to fix formaldehyde derived from methanol, as a carbon source. Moreover, hexose-6-phsophate synthase and 6-phosphohexulose isomerase are involved in such metabolic pathway of the methylotrophic microorganism.

In connection to this, said gene encoding the enzyme derived from the methylotrophic microorganism is introduced into *Burkholderia capacia* TM1, which is an organism not having the ability to utilize methanol, and the enzyme is over-expressed in the microorganism. Then it is reported that the intake of formaldehyde is increased and the metabolic pathway to generate formaldehyde by metabolism of vanillic acid is activated (Appl. Environ Microbiol. 2003). Such knowledge indicates that the ability to degrade vanillic acid can be also improved in a non-methylotrophic microorganism through the pathway of hexulose-6-phosphate synthase/6-phosphohexulose isomerase.

DISCLOSURE OF THE INVENTION

It is therefore an object of the present invention to provide a method to improve the ability to absorb formaldehyde in a plant, by introducing metabolic system of formaldehyde into the plant, for the purpose to decrease environmental concentration of formaldehyde. It is assumed that such plant has resistance to formaldehyde, therefore, it is also an object of the present invention to provide a method to enhance formaldehyde resistance in a plant. It is also an object of the present invention to expand such method to autotrophy in general, not only plant species.

Therefore, this invention provides a method to confer formaldehyde-resistance to an autotrophy comprising the steps of; introducing gene(s) encoding enzyme(s) involved in the metabolic system of formaldehyde into the autotrophy having the Calvin cycle and having the enzyme(s) involved in the metabolic system artificially expressed in the autotrophy, thereby formaldehyde-resistance is conferred to the autotrophy. Such transgenic autotrophy is also included within the range of this invention.

Moreover, this invention provides a method to have an autotrophy to absorb formaldehyde comprising the steps of; introducing gene(s) encoding enzyme(s) involved in the metabolic system of formaldehyde into the autotrophy having the Calvin cycle and having the enzyme(s) involved in the metabolic system artificially expressed, thereby the autotrophy is made to absorb formaldehyde. Such transgenic autotrophy is also included within the range of this invention.

Moreover, this invention provides a method to confer formaldehyde-resistance to a plant comprising the steps of; introducing genes encoding hexulose-6-phosphate synthase and 6-phosphohexulose isomerase into the plant and having the genes expressed in the chloroplast of the plant, thereby the ability to assimilate formaldehyde into an intermediate of the Calvin cycle is conferred to the plant. Such transgenic plant is also included within the range of this invention.

Moreover, this invention provides a method to have a plant to absorb environmental formaldehyde comprising the step of; introducing genes encoding hexulose-6-phosphate synthase and 6-phosphohexulose isomerase into the plant and having the genes expressed in the chloroplast of the plant, thereby the ability to assimilate formaldehyde into an intermediate of the Calvin cycle is conferred to the plant. Such transgenic plant is also included within the range of this invention.

According to the present invention, it became possible to produce a transgenic plant having a pathway to metabolize formaldehyde through the Calvin cycle, by introducing genes encoding hexulose-6-phosphate synthase and 6-phosphohexulose isomerase into the plant and having the genes expressed in the chloroplast of the plant. Such transgenic plant has resistance to environmental formaldehyde, and capable of reducing environmental formaldehyde significantly.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5 is a figure showing the sequences of the primer for the plasmid containing rmpA gene, the transit peptide, and rmpA gene (SEQ ID NOS: 2, 3, 5, 7, 8, and 9).

FIG. 6 is a figure showing the sequences of the primer for the plasmid containing rmpB gene, the transit peptide, and rmpB gene (SEQ ID NOS: 1, 4, 5, 6, 8, and 10).

BEST MODE FOR CARRYING OUT THE INVENTION

The present inventors found that the ability to assimilate formaldehyde to an intermediate of the Calvin cycle can be conferred to a plant, by introducing the gene encoding hexulose-phosphate synthase (hereafter, referred to HPS) and the gene encoding 6-phosphohexulose isomerase (hereafter, referred to PHI) into the plant.

That is, formaldehyde, which is a harmful chemical substance, can be incorporated into the Calvin cycle and assimilated, therefore, environmental formaldehyde can be absorbed into the plant and concentration of formaldehyde can be decreased. In other word, the transgenic plant according to this invention has a pathway to metabolize formaldehyde through the Calvin cycle, and thus the environmental formaldehyde can be treated. Moreover, it is assumed that such transgenic plant has resistance to formaldehyde.

Figure 1:
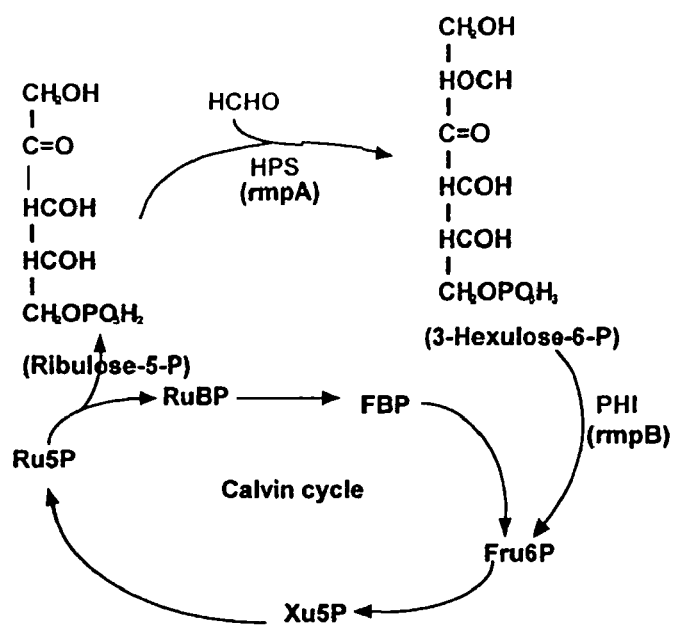
FIG. 1 is a figure showing the strategy to render the ability to assimilate formaldehyde by the method according to this invention.

The strategy of the present invention is shown in FIG. 1. Ribulose-5-phosphate (Ru5P), which is an intermediate of the Calvin cycle, binds to formaldehyde (HCHO) by the enzymatic reaction mediated by HPS, and 3-hexulose-phosphate is formed. Then the formed 3-hexulose-6-phosphate is converted to fructose-6-phosphate (Fru6P) by the action of PHI. Fru6P is also an intermediate of the Calvin cycle, therefore, formaldehyde is incorporated into the intermediate of the Calvin cycle consequently, and formaldehyde is assimilated through metabolic system of the Calvin cycle.

Meanwhile, in FIG. 1, RuBP means Ribulose-1,5-bisphosphate, FBP means fructose-1,6-bisphosphate and Xu5P means xylulose-5-phosphate. Moreover, rmpA means a gene encoding HPS, rmpB means a gene encoding PHI, and a DNA construct containing these genes was constructed. The strategy to construct the plasmid containing said rmpA gene and said rmpB gene will be described in detail in the following Examples.

In a transgenic plant over-expressing these enzymes by introduction of the HPS gene and the PHI gene, the ability to treat environmental formaldehyde enhanced. The most prominent feature of this invention lies in that a novel metabolic pathway to metabolize formaldehyde through the Calvin cycle is provided, by expressing the HPS and the PHI. Various modifications can be made within the range of this invention as described and present invention can be performed properly.

As described in detail in the following Examples, such transgenic plant was effective to decrease the concentration of formaldehyde in the atmosphere. Moreover, such transgenic plant exhibited resistance against formaldehyde. Meanwhile, the amino acid sequences of the enzymes involved in this invention (i.e. HPS and PHI) and the nucleotide sequences encoding these enzymes have been known so far (accession No.: AB034913).

Therefore, it is assumed that the technique according to this invention that enables reduction of environmental formaldehyde can be applied for many purposes. For example, the HPS gene and the PHI gene can be introduced into foliage plants, garden plants or street trees. Such transgenic plants are useful to decrease the environmental pollutants in the atmosphere, soil and water (phytoremediation). In addition, the transgenic plant according to this invention is useful for the treatment of residual formaldehyde utilized in agricultural industry, fishing industry and industry etc.

For the purpose to produce the transgenic plant according to this invention, a DNA construct for expression of the HPS gene, and a DNA construct for expression of the PHI gene are constructed. Of course, such DNA construct harbors gene encoding HPS or gene encoding PHI. In addition, at the upstream of these genes, the DNA construct also harbors a promoter sequence to enhance the expression of the genes in the plant, a transit peptide to have the genes expressed at a desired site (e.g. chloroplast), and a gene involved in drug resistance which is used for selection of the transgenic plant by the drug resistance. The method according to this invention utilizes the Calvin cycle that relates to photosynthesis, therefore, expression of HPS and PHI in the chloroplast is a preferred embodiment according to this invention.

The promoter to be utilized is not particularly limited, however, PrbcS used in the following Examples is particularly preferable, because it has potent efficacy and its efficacy exhibits high relationship with photosynthesis. Despite of it, various other promoters conventionally utilized in this technical art can be also adopted. Moreover, the drug resistance gene to be utilized is not particularly limited, gentamicin resistant gene and kanamycin resistant gene utilized in the Examples are preferred, and various other drug resistance genes conventionally utilized in this technical art can be also adopted. Meanwhile, these drug resistance genes are useful for the selection of transformants. However, considering that diffusion of antibiotic resistance is not socially preferable, it is desired that the drug resistance be removed when the transformants are put into the market.

The DNA construct described above can be introduced into bud or callus of a plant for transformation. As the method for transformation, various methods such as *agrobacterium* method, protoplast method, PEG method, electroporation method and particle gun method have been known. As a preferred embodiment, *agrobacterium* EHA101 pMP90 is utilized in the following Examples, various methods for gene introduction can be utilized ad libitum. Then, transformants in which the gene is introduced can be selected using the drug resistance as the index, to obtain the transformants. In addition, the expression of an exogenous gene is not high in general. However, the expression of the genes encoding HPS and PHI can be enhanced due to the promoter inserted into these constructs, and these genes can exert their effects.

Here, the target plant of gene introduction is not particularly limited. In the following Examples, the genes encoding the enzymes are introduced into *Arabidopsis thaliana* and tobacco as the representative plants. However, the genes encoding HPS and PHI can be introduced into various other plants in the same manner, and the ability to remove and/or absorb formaldehyde can be rendered to the plant, which is understood by a skilled artisan. A plant belonging to Solanaceae, Cruciferae and various other dicotyledonous plans can be included in the preferred plant, however, the species of the plants are not limited to them, and present invention can be applied to e.g. monocotyledonous, theoretically.

As concrete examples of the plant, pothos, pachira, benjamin, concinna, crest gold, sansevieria can be listed as a foliage plant and gardening plant, however, it is not to be limited to them. Moreover, cherry tree, zelkova, maidenhair tree, plane tree, saddletree, poplar, maple tree can be listed as a street tree, however, it is not to be limited to them.

Moreover, it is assumed that application of the method according to this invention is not limited to only plants, and the method can be generally applied to autotrophy having the Calvin cycle. Here, the autotrophy means an organism having photosynthetic function or a function similar to it, which is capable of producing organic compounds from $H_2O$ and $CO_2$, and it is intended to exclude heterotrophic organisms. As concrete Examples of such organism, in addition to plants in general, photosynthetic bacteria, cyanobacteria, and algae can be listed. As these autotrophies have the Calvin cycle, the ability to assimilate formaldehyde can be rendered to these organisms using same strategies.

As a concrete means to metabolize formaldehyde through the Calvin cycle, it is preferred to introduce the genes encoding HPS and PHI into a plant, as performed in the following Examples. However, the means to achieve this invention is not necessarily limited to introduction of the genes encoding said enzymes.

For example, methylotrophic yeasts have dihydroxyacetone synthase (DHAS) and dihydroxyacetone kinase. Owing to the function of these enzymes derived from the yeast, formaldehyde can be fixed to xylose-5-phosphate to produce dihydroxyacetone-3-phosphate and 3-phosphoglyceric acid. In this reaction, both of the substrates and the products are approximately identical to the intermediates of the Calvin cycle, therefore, it is assumed that such knowledge may be also utilized to achieve this invention.

That is, as other genes encoding enzymes that can be utilized in this invention, genes encoding dihydroxyacetone synthase (DAS1) and dihydroxyacetone kinase (DAK1) can be combined and the combination can be also adopted. As described above, in this case, reaction of xylose-5-phosphate and formaldehyde are catalyzed by dihydroxyacetone synthase, and 3-phosphoglyceric acid and dihydroxyacetone are produced. The latter product is converted to dihydroxyacetone-3-phosphate by enzymatic reaction catalyzed by dihydroxyacetone kinase (DHAK), and then the product is incorporated into metabolic system through the Calvin cycle. According to this invention, such embodiment can be also performed.

Such embodiment is also within the range of this invention. In this specification, "gene encoding enzymes involved in the metabolic system of formaldehyde" is not limited to genes encoding HPS and PHI, and it is intended to include other genes encoding enzymes available to metabolize formaldehyde and to incorporate the metabolite into the Calvin cycle.

EXAMPLES

Example 1

Analysis Using *Arabidopsis thaliana*

(Construction of the Construct)

Figure 2:
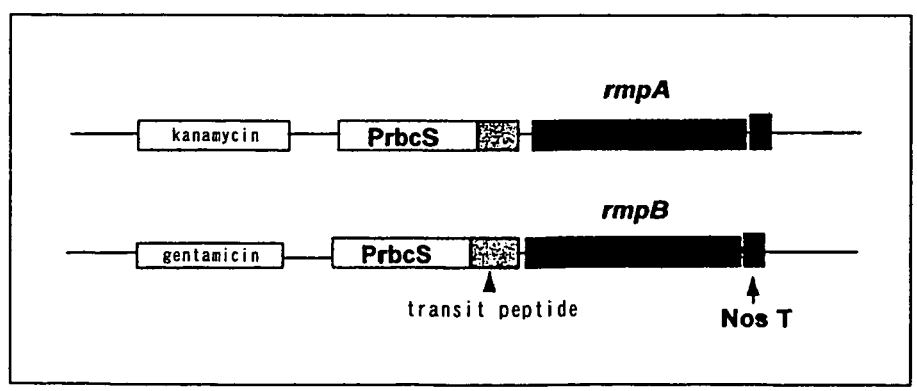
FIG. 2 is a figure showing the structures of the DNA construct containing rmpA gene and that containing rmpB gene used in the examples.

In *Arabidopsis thaliana*, as a vector for expression of HPS and PHI, a DNA construct was produced and it contained the gene encoding HPS (rmpA) and the gene encoding PHI (rmpB). The structures of the two DNA constructs produced are shown in FIG. 2. Meanwhile, in addition to the genes encoding HPS and PHI, a transit peptide to have HPS and PHI expressed in chloroplast, and drug resistance genes (kanamycin resistance gene, gentamicin resistance gene) for selection of the transformant were also inserted into the construct.

Figure 3:
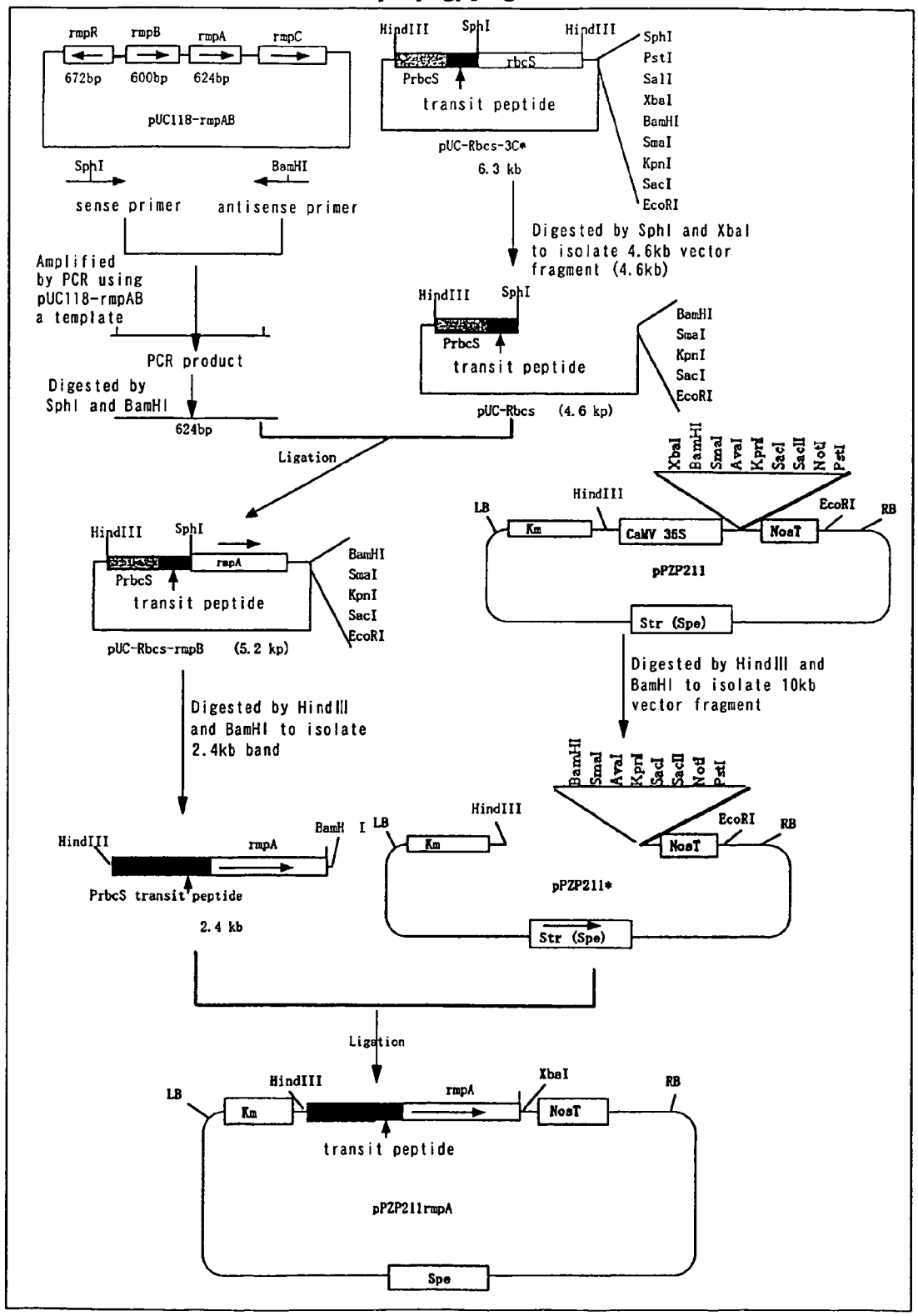
FIG. 3 is a figure showing the strategy to construct the plasmid containing rmpA gene.
Figure 4:
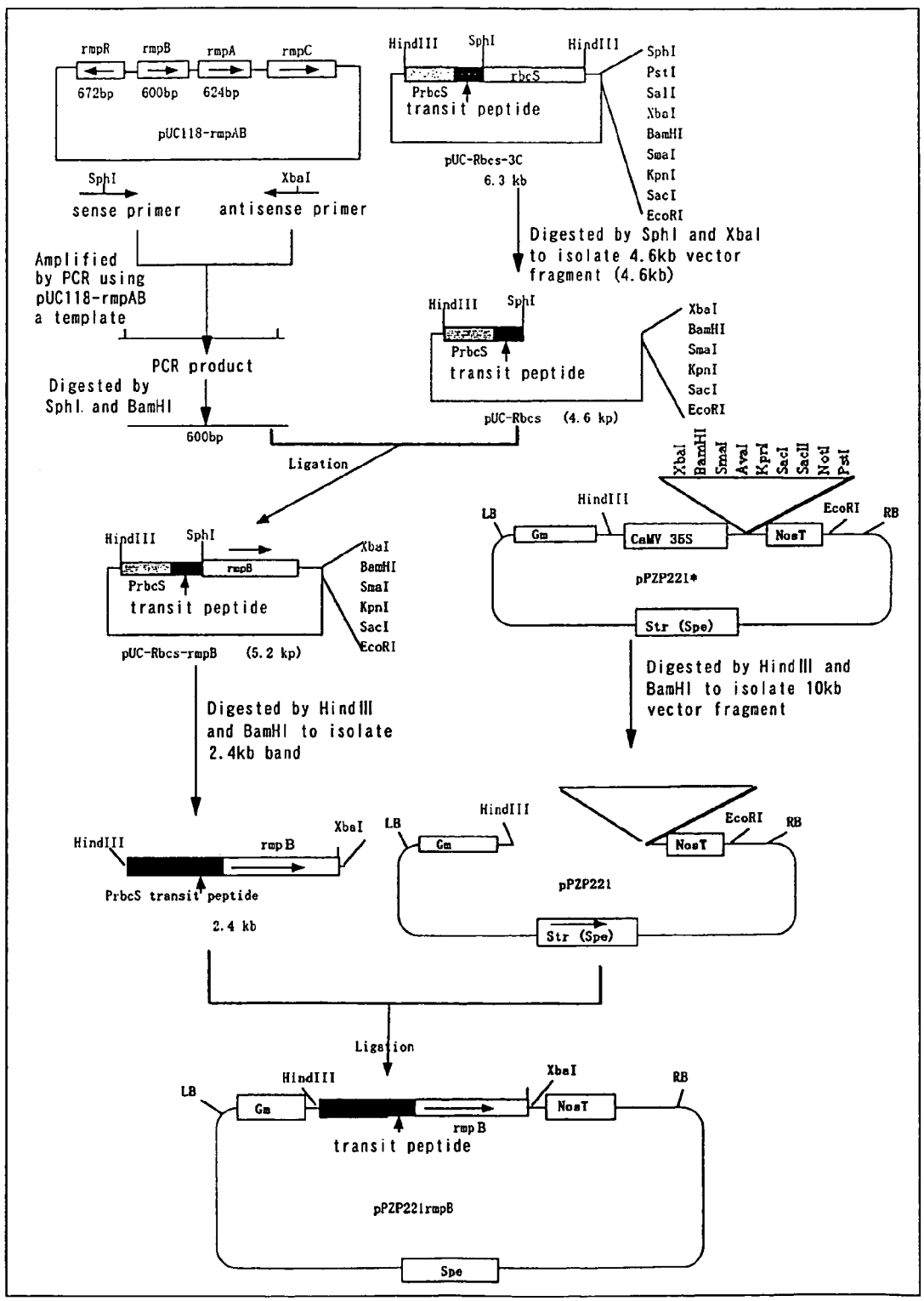
FIG. 4 is a figure showing the strategy to construct the plasmid containing rmpB gene.

Then the strategies for production of the construct for expression of HPS containing rmpA gene, and the construct for expression of PHI containing rmpB gene are shown in FIG. 3 and FIG. 4. The rmpA gene and the rmpB gene are located within an identical operon of *Mycobacterium gastri* MB19, which is a methylotrophic bacterium of *Mycobacterium*. As well, the bacteria is a prokaryotic organism and the promoter from the bacteria can not operate in a plant body. Therefore, only the coding regions of rmpA gene and rmpB gene were obtained, and the chimeric gene containing the plant promoter for transformation was constructed.

The rmpA gene was amplified by PCR (rmpA sense GCTTGCAAGGGGTAACCATGACG: SEQ ID NO.1, rmpA antisense: TCTAGAGGATCAGGCGATCGC: SEQ ID NO.2), and the PCR product and Puc-Rbcs-3C were digested by SphI and BamHI. The isolated rmpA gene of 624 bp and the vector fragment of 4.6 kb were isolated, rmpA gene was ligated to the vector, to produce pUC-RbcS-rmpA plasmid. The pUC-RbcS-rmpA and binary vector pPZP221 were digested, RbcS-rmpA insert of 2.4 kb and vector band pPZP211 were isolated, and they were ligated to produce pPZP221 rmpA plasmid.

Here, the portion utilized as the sequence of transit peptide was nucleotide number 298-468 of accession No: X05986, and the portion utilized as the sequence of the rpmA gene was nucleotide number 2518-2150 of accession No: AB034913. The sequences of the primer, the transit peptide, and rmpA gene of the construct are shown in FIG. 5.

Moreover, rmpB gene was amplified by PCR (rmpB sense GCTTGCAAGGGGTAACCATGACG: SEQ ID NO.3, rmpB antisense: TCTAGATCCGGGTCACTCGAG: SEQ ID NO.4), and the PCR product and pUC-Rbcs-3C were digested by SphI and XbaI. The isolated rmpB gene of 600 bp and the vector fragment of 4.6 kb were isolated, and the rmpB gene was ligated to the vector to produce pUC-RbcS-rmpB plasmid. The to pUC-RbcS-rmpB and binary vector pPZP221 were digested by HindIII and XbaI, pRbcS-rmpB insert of 2.4 kb and the vector band pPZP221 of 10 kb were isolated, and they were ligated to produce pPZP221 rmpB plasmid.

Here, the portion utilized as the transit peptide sequence was nucleotide number 298-468 of accession No: X05986, and the portion utilized as the rpmB gene sequence was nucleotide number 1845-2456 of accession No: AB034913. The sequences of the primer, the transit peptide, and rmpB gene of the construct are shown in FIG. 6.

(Selection of the Transformants)

Using the plasmid thus constructed, *Arabidopsis thaliana* was transformed by *Agrobacterium* method. In concrete, *Arabidopsis thaliana* was transformed by rmpA, and the transformant was selected by kanamycin resistance introduced together with the rmpA. Afterward, the transformed plant was further transformed by rmpB, and the transformant was selected by gentamicin resistance introduceded together with the rmpB. By this way, transformants introduced with both of rmpA gene and rmpB gene were selected. Conversely, *Arabidopsis thaliana* was transformed by rmpB and the transformant was selected by gentamicin resistance introduced together with the rmpB. Afterward, the transformed plant was further transformed by rmpA, and the transformant was selected by kanamycin resistance introduced together with the rmpA. By this way, the transformants introduced with both of the rmpA gene and the rmpB gene were selected.

(Confirmation of the Introduced Gene)

Then, as to the transformant of *Arabidopsis thaliana* thus produced, incorporation of the gene was investigated by RT-PCR and northern blot analysis. As the result, by treating with the construct containing rmpA gene and rmpB gene, it was confirmed that both genes were introduced into the transformants thus obtained. Moreover, it was further confirmed whether or not the expression of enzymatic proteins encoded by the genes could be observed, by western blotting analysis using an antibody against HPS. As the result, the expression of HPS protein derived from rpmA gene was confirmed.

(Resistance Against Formaldehyde)

Figure 7:
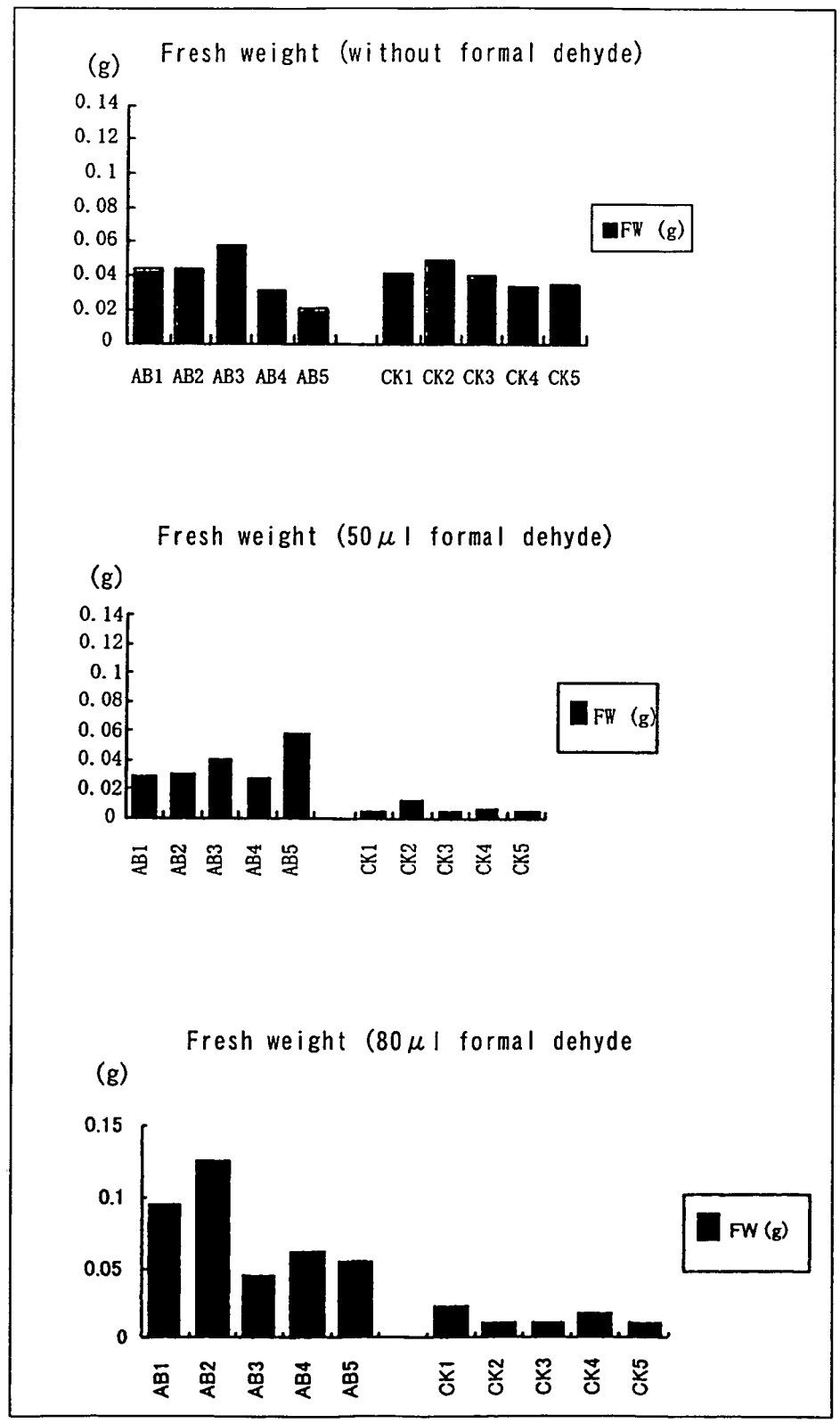
FIG. 7 is a graph showing the effect of formaldehyde on the fresh weights of the plant bodies of the transgenic plant and the control plant of *Arabidopsis thaliana*.

The formaldehyde resistance of the transgenic plants introduced with these genes (rpmA, rpmB) was investigated by the fresh weights of the plant bodies (FIG. 7). After selection by antibiotics, the seedlings were transferred to agar medium not containing antibiotics, and they were grown for one week. After that, the seedlings were transferred to agar medium added with 50 µl formaldehyde (37%) per 100 ml, the fresh weights were measured after they were grown for 4 to 5 weeks. In FIG. 7, the upper panel shows the result obtained from agar medium not added with formaldehyde, the middle panel shows the result obtained from agar medium added with 50 µl formaldehyde, the lower panel shows the result obtained by agar medium added with 80 µl formaldehyde. Moreover, in FIG. 7, AB1 to AB5 show transgenic plants introduced with the both genes (rmpA and rmpB), and CK1 to CK5 show the control plants.

As a result, as to the fresh weights of the plant bodies under the circumstance not containing formaldehyde, no difference was observed between the control group (CK1-CK5) and the transformant group introduced with the genes of both enzymes (AB1-AB5) (upper panel). Meanwhile, the transformants grew well (AB1-AB5) under the circumstance containing formaldehyde, however, plant growth was inhibited in the controls (CK1-CK5). Then difference was observed on the fresh weights of the plant bodies (middle panel, lower panel). This result indicates that the transformants have resistance to formaldehyde.

(Measurement of Enzymatic Activity)

The enzymatic activities of HPS and PHI were measured by spectroscopic method at 30° C. In concrete, ribose-5-phosphate was used as the starting substrate, NADPH was produced through enzymatic reaction by HPS and PHI by formaldehyde dependent manner, and the produced NADPH was detected at 340 nm to measure the enzymatic activity. In short, pre-incubation was performed for 2-3 minutes at 30° C., protein extract and 50 µl formaldehyde (50 mM) were added to it, and enzymatic reaction was performed in the reaction mixture described below. The formulation of the to mixture for the enzymatic reaction per 1 ml is as follows.

| | |
|---|---|
| KPB (Potassium phosphate buffer), pH 7.5 | 50 mM |
| $MgCl_2$ | 2.5 mM |
| Ri5P (Ribose-5-phosphate) | 2.5 mM |
| HCHO (formaldehyde) | 2.5 mM |
| $NADP^+$ | 2.5 mM |
| PRI (Phosphoriboisomerase) | 10 U/ml |
| PGI (Phosphoglucoisomerase) | 10 U/ml |
| GDH (Glucosephosphate dehydrogenase) | 10 U/ml |
| HPS (3-Hexulose-6-phosphate synthase) | 10 U/ml |
| | (Plant protein extract 0.05 ml) |
| PHI (6-Phosphohexulose isomerase) | 10 U/ml |
| | (Plant protein extract 0.05 ml) |
| $dH_2O$ | 0.55 ml |

Meanwhile in this reaction solution, authentic PHI was used when enzymatic activity of PHI was measured, and authentic HPS was used when enzymatic activity of HPS was measured.

Figure 8:
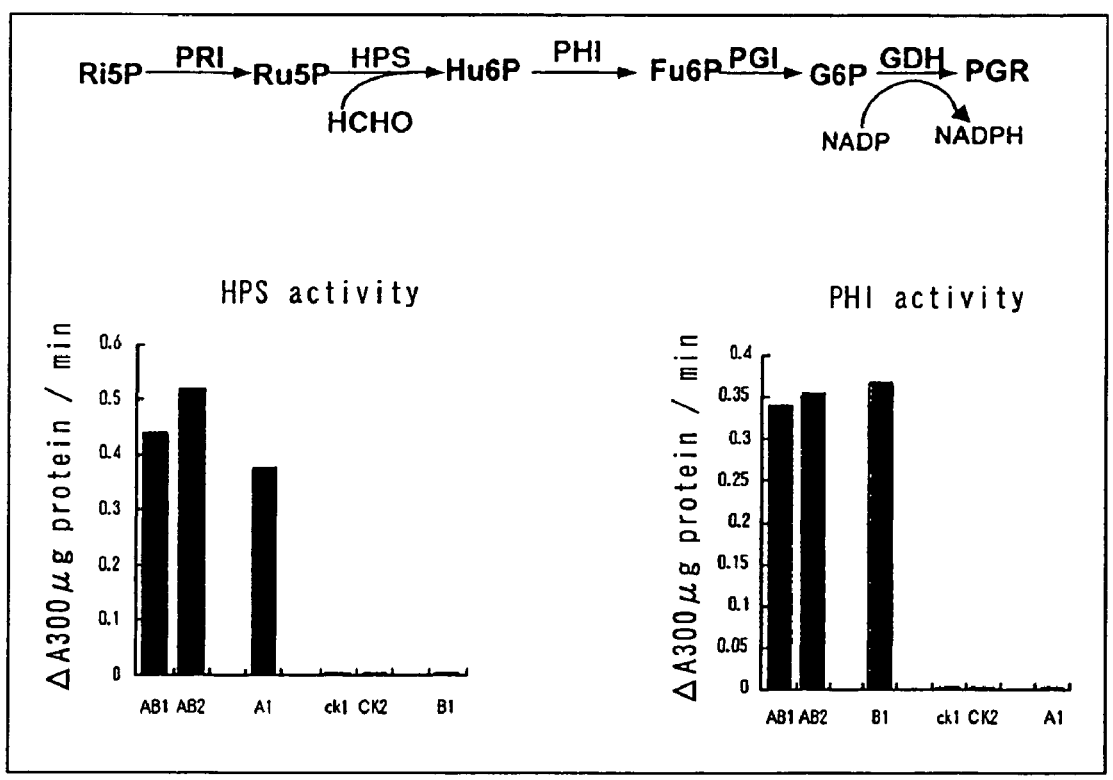
FIG. 8 is a graph showing the HPS activity and the PHI activity, evaluated on the transgenic plant and the control plant of *Arabidopsis thaliana*.

The HPS activity and the PHI activity measured by the method are shown in FIG. 8 (FIG. 8 left panel: HPS activity, right panel: PHI activity). As well, the principle of the assay for measurement of the enzymatic activity is shown in the upper panel of FIG. 8. AB1 and AB2 were introduced with the both of rmpA gene and rmpB gene, and enzymatic activities of the both enzymes were detected in AB1 and AB2, as shown in FIG. 8. Moreover, A1 was introduced with rmpA gene and only HPS activity was detected in A1, and A2 was introduced with rmpB gene and only PHI activity was detected in A2.

(Intake of Formaldehyde)

The seedlings of *Arabidopsis thaliana* (20 plants for each group) were transferred into plant boxes (370 ml), they were grown for 3 to 4 weeks until reaching to their bolting stage. Thereafter, 50 µl of formaldehyde (37%) was added to 1.5 ml micro-tubes and they were set at the corner of the plant boxes.

Three to four weeks later, the covers of the plant boxes were changed to new ones having apertures in the middle of the covers. Formaldehyde detectors were set at the apertures and intake of formaldehyde was detected. The measurement was stopped 3.5 hours after setting of the detectors, and photographs were taken.

Figure 9:
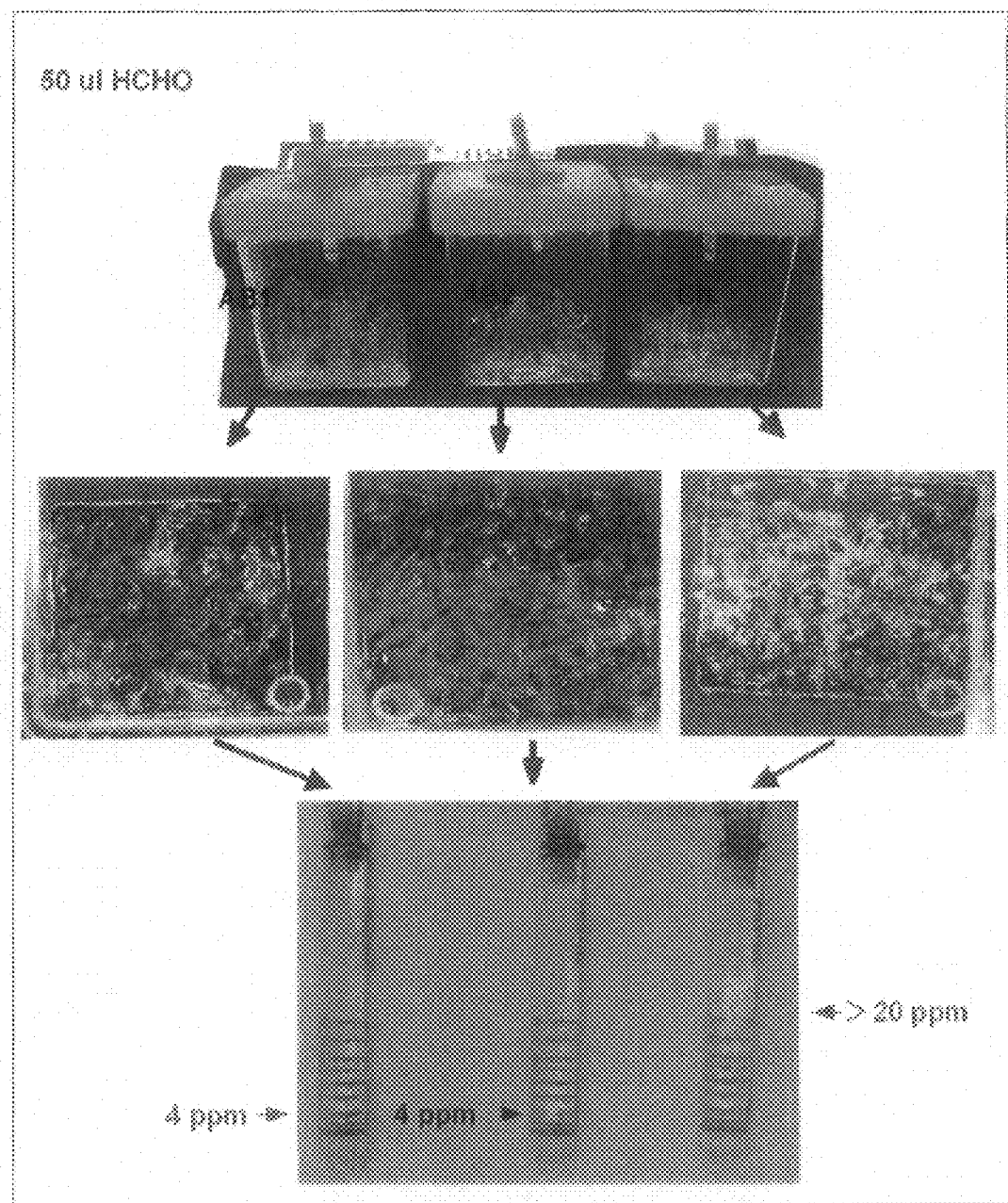
FIG. 9 is a photograph showing formaldehyde resistance and formaldehyde intake, evaluated on the transgenic plant and the control plant to of *Arabidopsis thaliana*.

The results of the transformants (AB1: left panel, AB2: middle panel), as well as the result of the control (CK: right panel, the plant body transformed by an empty vector not containing HPS gene or PHI gene) were shown in FIG. 9. From the photograph of FIG. 9, it was shown that the seedlings of the transformants grew well, whereas the growth was inhibited in the control, indicating that the transformants exhibit formaldehyde resistance. Moreover, concentration of formaldehyde detected after 3.5 hours was approximately 4 ppm for AB1 and AB2, on the other hand, the formaldehyde concentration detected for the control plant was above 20 ppm. This result indicates that formaldehyde in the atmosphere was absorbed by AB 1 and AB2. Meanwhile, the amount of formaldehyde detected by the detector varies in proportion to the detection time, therefore, one can obtain the actual formaldehyde concentration by dividing the value detected from the detector with the detection time.

Furthermore, the intake of formaldehyde in the water solution was also investigated. After selection by antibiotics, seedling was grown two weeks on MS agar medium not containing antibiotics. The plant body (0.3 g) was immersed into 10 ml formaldehyde solution, and formaldehyde concentration in the solution was measured after 30 hours.

Figure 10:
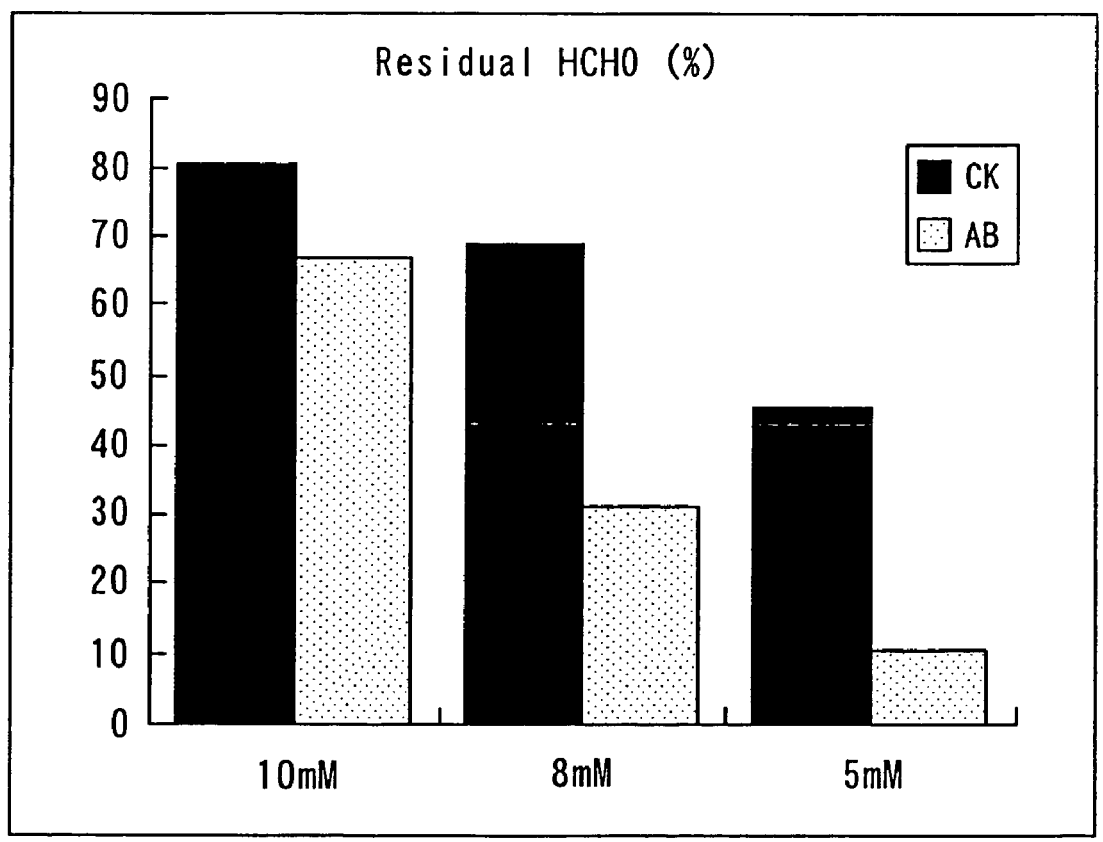
FIG. 10 is a graph showing the ratio of intake of liquid formaldehyde in the transgenic plant and in the control plant of *Arabidopsis thaliana*.

As the result, it was observed that the concentration of formaldehyde decreased significantly in the transformant (AB: right column), compared with the control (CK: left column) (FIG. 10). In FIG. 10, the vertical axis indicates the ratio of residual formaldehyde. Especially, when the initial concentration of formaldehyde is 5 mM, the ratio of residual formaldehyde decreased to approximately 10%, suggesting significant difference compared with the control. This result also indicates that the transformant intakes formaldehyde.

Example 2

Analysis Using Tobacco (Incorporation of Gene and its Confirmation)

In the same way as experiments using *Arabidopsis thaliana*, rmpA gene and rmpB gene were introduced into tabacco to produce transformed tobacco. Investigation was made on PCR and northern analysis, and in the transgenic plant introduced with rmpA gene and rmpB gene, the existence of both genes was confirmed. In addition, the expression of protein caused by the introduced gene was confirmed by western blot analysis, and expression of HPS protein caused by rmpA gene was also confirmed.

(Measurement of Enzymatic Activity)

Figure 11:
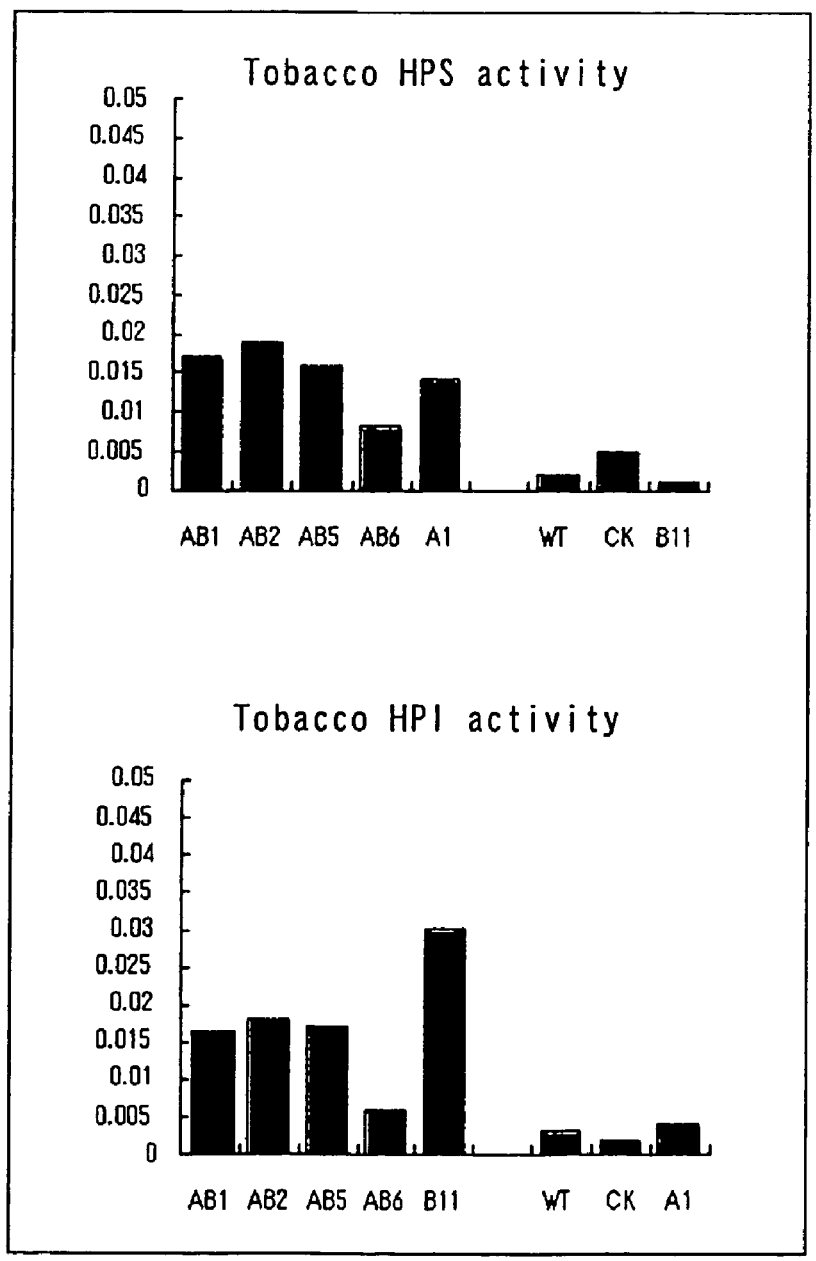
FIG. 11 is a graph showing the HPS activity and the PHI activity, evaluated on the transgenic plant and the control plant of tobacco.

The enzymatic activities of HPS and PHI observed in the transgenic tobacco plant thus produced are shown in FIG. 11 (upper panel: HPS activity, lower panel: PHI activity). Both of rmpA gene and rmpB gene were introduced in AB2, AB5 and AB6, therefore, both of the HPS and PHI enzymatic activities were detected in them. Moreover, the enzymatic activities of HPS and PHI were low in the wild-type (WT) and the control (CK).

(Intake of Formaldehyde)

The transgenic tobacco was proliferated by cuttage, then they were transferred to agar medium not containing antibiotics for root growth. Two weeks later, 100 µl of formaldehyde (37%) was put in a plant box (370 ml) and formaldehyde was allowed to evaporate into the air. Two months later, The formaldehyde detector was set like the case of *Arabidopsis thaliana*, the measurement was stopped four hours later from the setting, and photograph was taken.

Figure 12:
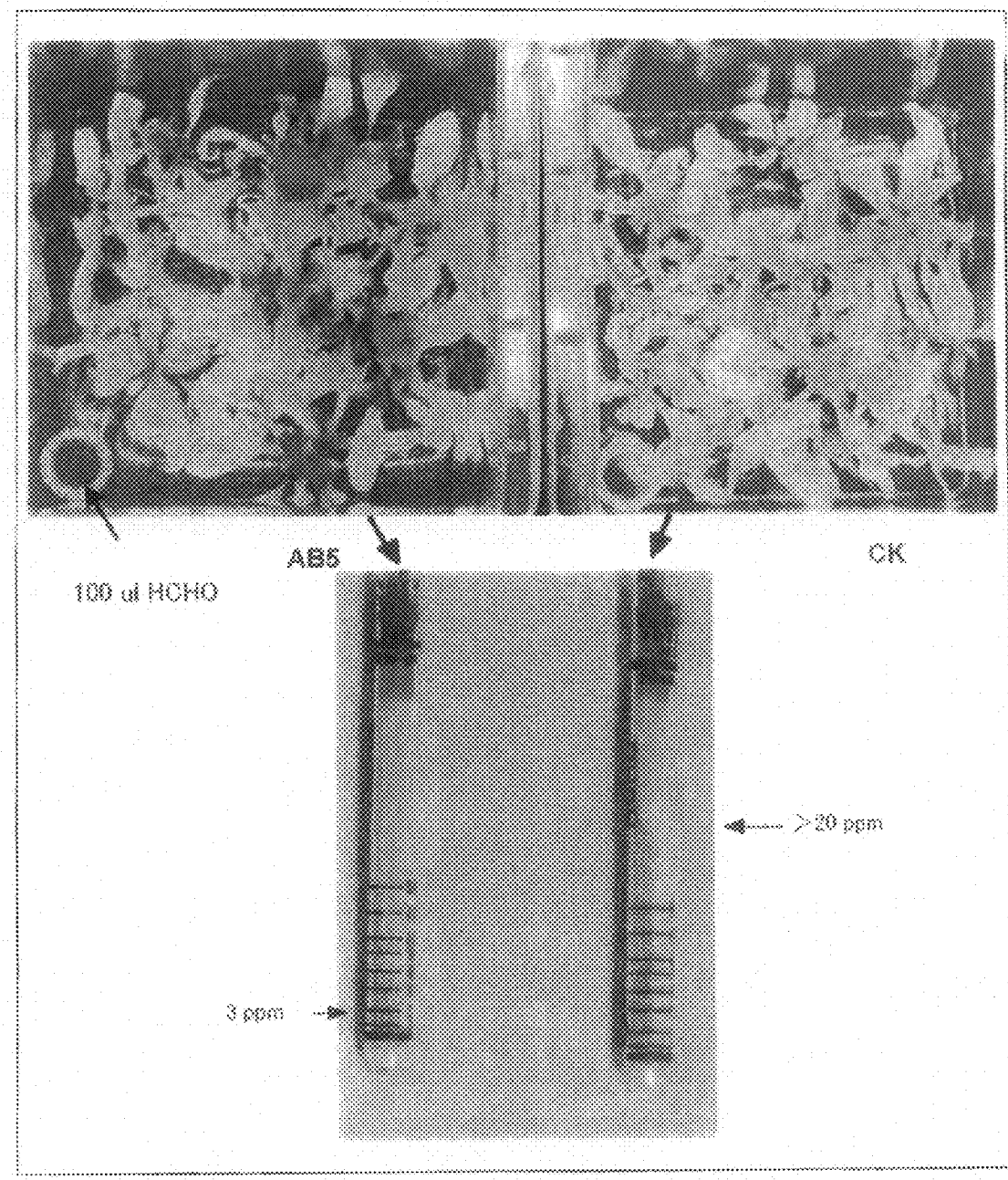
FIG. 12 is a photograph showing formaldehyde resistance and formaldehyde intake, evaluated on the transgenic plant and the control plant of tobacco.

The result obtained on AB5 (transformant: left side) and that obtained on CK (control: right side) were shown in FIG. 12. From the photograph of FIG. 12, it was shown that the seedling grew well in the transformant, whereas inhibition of growth was observed in the control, indicating that the transformant was resistant to formaldehyde. Furthermore, the degree of coloring was evaluated 4 hours later from the setting, and the formaldehyde concentration in the plant box was estimated to be approximately 3 ppm for AB5. On the other hand, the concentration was estimated to be higher than 20 ppm for the control plant. From the difference, it was confirmed that AB5 absorbed formaldehyde in the atmosphere.

(Resistance Against Formaldehyde)

Figure 13:
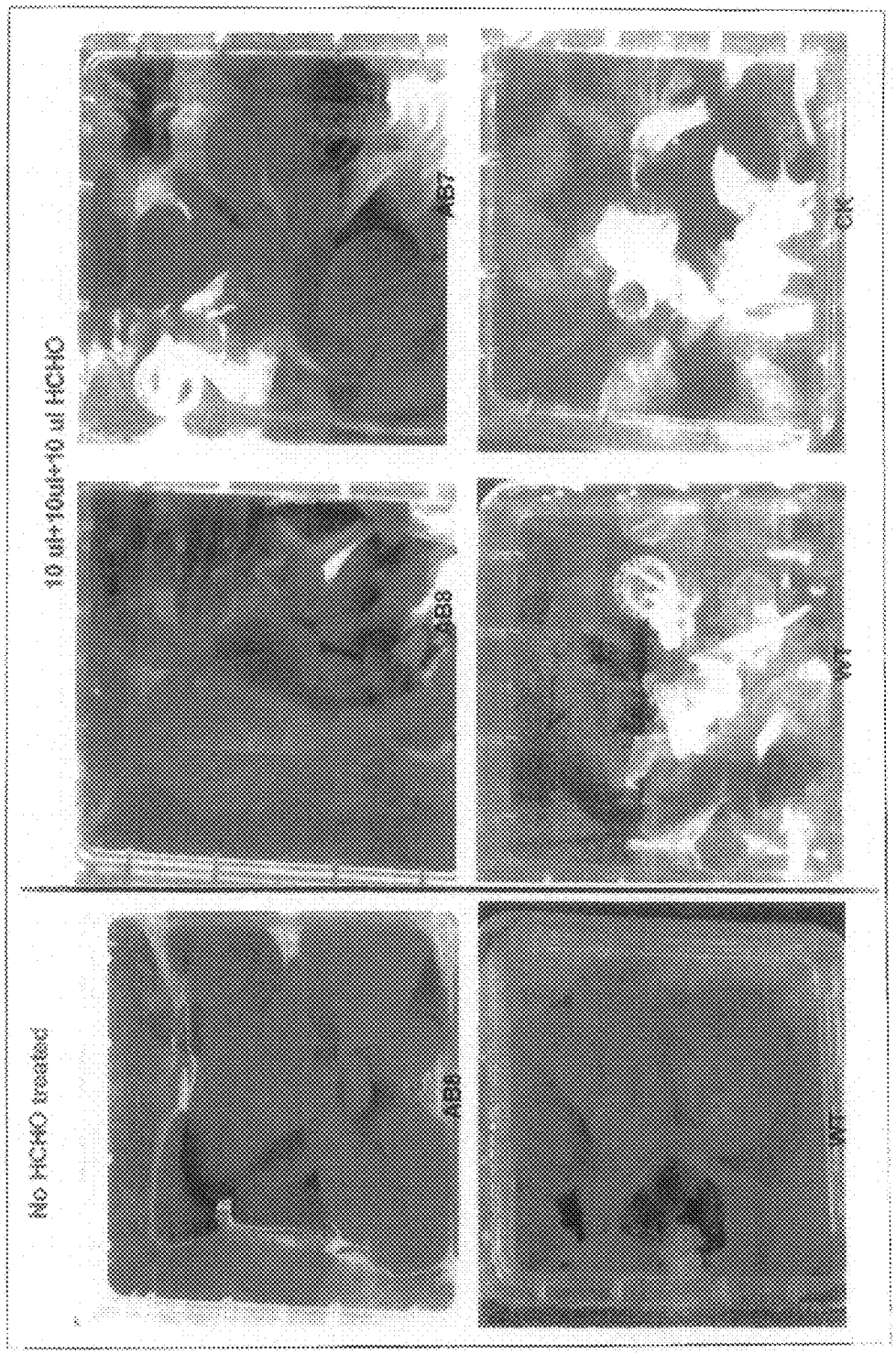
FIG. 13 is a photograph showing resistance against formaldehyde, evaluated on the transgenic plant and the control plant of tobacco.

After selection by antibiotics, seedlings of the transgenic tobacco was transferred onto MS medium not containing antibiotics, then grown for one week. Ten µl of 37% formaldehyde was added into a micro-tube and it was put into plant box. Two weeks later, 10 µl formaldehyde was re-supplied to the same micro-tube. This procedure was repeated twice after another two weeks. The plant was grown for 4 weeks and photograph was taken after the growth (FIG. 13). In FIG. 13, the upper photographs represent the transformants, and the lower photographs represent the wild-type plants or control plants. As the result, the effect of formaldehyde treatment was not recognized in the transformants (AB7, AB8), and no difference was observed from the non-treated group (FIG. 13: left side of the upper panel). On the other hand, compared with the non-treated group, significant growth inhibition was observed in the wild-type (WT) and in the control (CK) (FIG. 13: middle and right side of the lower panel).

(Effect of Formaldehyde on the Root Growth of Tobacco Plant)

Figure 14:
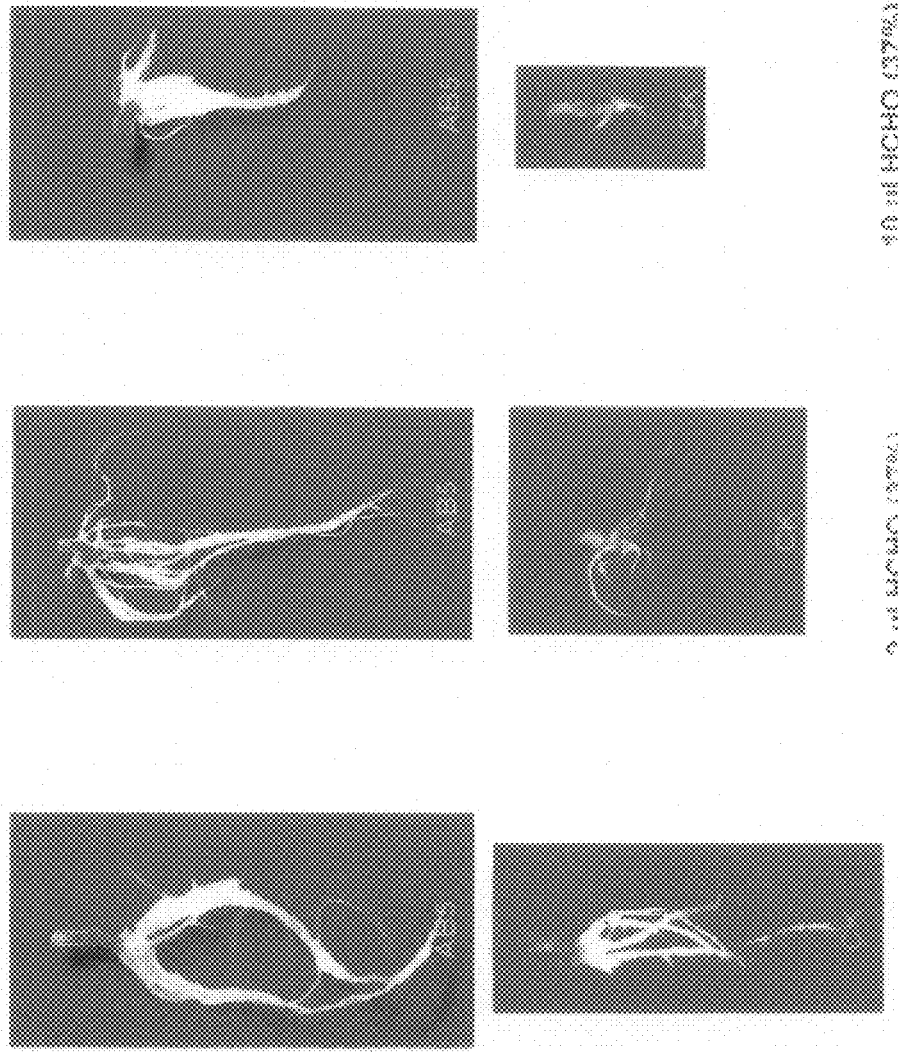
FIG. 14 is a photograph showing the effect of formaldehyde on the root growth of the transgenic plant and the control plant of tobacco.

After selection by antibiotics, seedlings of transformants was transferred onto MS medium not containing antibiotics, and grown for one week. Formaldehyde was added into a micro-tube and it was placed in the plant box. Two weeks later, the plants were removed from the box, and the effect of formaldehyde exerted on the growth of root was investigated (FIG. 14). As the result, treatment by 2 µl formaldehyde (37%) did not effect on the root growth of the transgenic plant (AB5), and root growth was recognized even under treatment by 10 µl formaldehyde (37%) (FIG. 14: upper panel). On the other hand, root growth of the control plant (CK) was significantly inhibited, under treatment by 2 µl formaldehyde (37%) (FIG. 14: lower panel).

(Investigation on the Crossed Line of the Plant)

Figure 15:
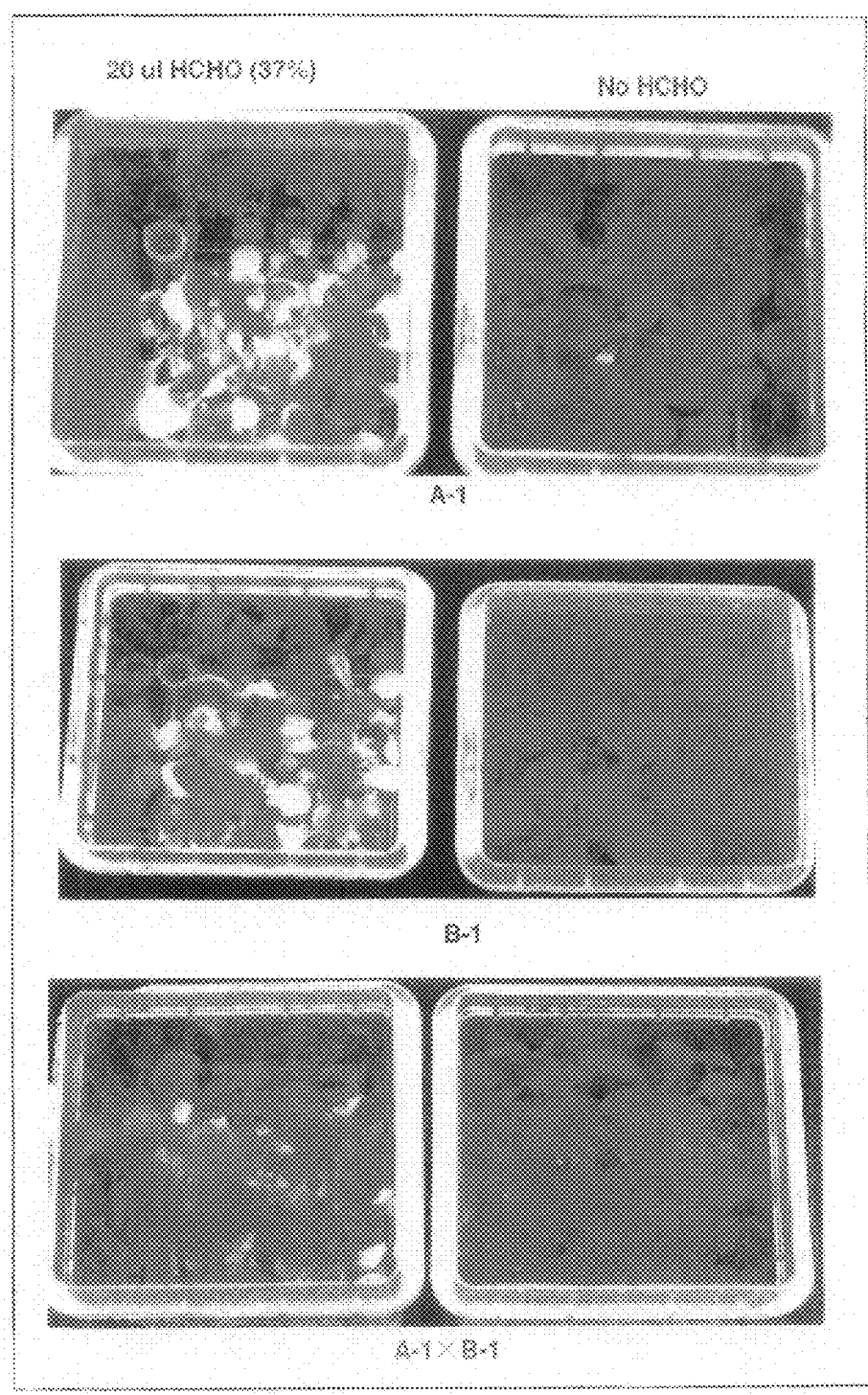
FIG. 15 is a photograph showing formaldehyde resistance in the plant line expressing rmpA gene (A-1), in the plant line expressing rmpB gene (B-1), and in the crossbred line of them (A-1X B-1).

The plant line expressing rmpA gene (A-1) and that expressing rmpB gene (B-1) were intercrossed (A-1X B-1), and the seeds of the crossed plant were obtained. It was grown 3 weeks on agar medium not containing antibiotics, photograph was taken after 4 weeks (FIG. 15). The samples treated by 20 µl fmaldehyde were shown in the left side, and those not treated by formaldehyde were shown in the right side.

As the result, in the A-1 line (FIG. 15: upper panel) expressing only HPS and in the B-1 line (FIG. 15: middle panel) expressing only PHI, inhibition in growth was observed when treated by 20 µl formaldehyde (37%). On the other side, in A-1X B-1 (FIG. 15: lower side) which is assumed to be expressing both enzymes, growth was not effected by formaldehyde treatment. Therefore, it was confirmed that simultaneous expression of both of A-1 and B-1 was required to obtain formaldehyde resistance.

INDUSTRIAL APPLICABILITY

According to this invention, by introducing genes encoding hexulose-6-phosphate synthase and 6-phosphohexulose isomerase into a plant to have the genes expressed in the chloroplast of the plant, a transgenic plant having a pathway to metabolize formaldehyde through the Calvin cycle is provided. The transgenic plant according to this invention has resistance against formaldehyde and is capable of reducing the level of environmental formaldehyde significantly. Therefore, it is assumed that the transgenic plant according to this invention can be used to purify environmental condition, by placing it in a residence or in an office.

The invention claimed is:

1. A method to confer formaldehyde resistance to a plant comprising the steps of; introducing genes encoding hexulose-6-phosphate synthase and 6-phosphohexulose isomerase into the plant and having the genes expressed in the chloroplast of the plant, thereby the ability to assimilate formaldehyde into an intermediate of the Calvin cycle is conferred to the plant.

2. The method according to claim 1 comprising the steps of; generating 3-hexulose-6-phosphate from ribulose-5-phosphate and formaldehyde by the action of said hexulose-6-phosphate synthase, and further converting the 3-hexulose-6-phosphate into fructose-6-phosphate by the action of said 6-phosphohexulose isomerase.

3. A transgenic plant having resistance against formaldehyde, in which genes encoding hexulose-6-phosphate synthase and 6-phosphohexulose isomerase are introduced into the plant to have the genes expressed in the chloroplast of the plant, thereby the ability to assimilate formaldehyde into an intermediate of Calvin cycle is rendered to the plant.

4. The transgenic plant according to claim 3, wherein said plant is a dicotyledonous plant.

5. The transgenic plant according to claim 4, wherein said plant is a plant of Solanaceae.

6. The transgenic plant according to claim 5, wherein said plant is tobacco.

7. The transgenic plant according to claim 4, wherein said plant is a plant of Cruciferae.

8. The transgenic plant according to claim 7, wherein said plant is *Arabidopsis thaliana*.

9. A method to have a plant to absorb environmental formaldehyde comprising the steps of; introducing genes encoding hexulose-6-phosphate synthase and 6-phosphohexulose isomerase into the plant and having the genes expressed in the chloroplast of the plant, thereby the ability to assimilate formaldehyde into an intermediate of the Calvin cycle is conferred to the plant.

10. The method according to claim 9 comprising the steps of; generating 3-hexulose-6-phosphate from ribulose-5-phosphate and formaldehyde by the action of said hexulose-6-phosphate synthase, and further converting the 3-hexulose-6-phosphate into fructose-6-phosphate by the action of said 6-phosphohexulose isomerase.

11. A transgenic plant having the ability to absorb formaldehyde, in which genes encoding hexulose-6-phosphate synthase and 6-phosphohexulose isomerase are introduced into the plant to have the genes expressed in the chloroplast of the plant, thereby the ability to assimilate formaldehyde into an intermediate of the Calvin cycle is conferred to the plant.

12. The transgenic plant according to claim 11, wherein said plant is a dicotyledonous plant.

13. The transgenic plant according to claim 12, wherein said plant is a plant of *Solanaceae*.

14. The transgenic plant according to claim 13, wherein said plant is tobacco.

15. The transgenic plant according to claim 12, wherein said plant is a plant of *Cruciferae*.

16. The transgenic plant according to claim 15, wherein said plant is *Arabidopsis thaliana*.

* * * * *